(12) United States Patent
Biza et al.

(10) Patent No.: US 9,943,541 B2
(45) Date of Patent: Apr. 17, 2018

(54) COMPOSITIONS AND METHODS FOR TREATING WATER

(71) Applicant: IMERYS PIGMENTS, INC., Roswell, GA (US)

(72) Inventors: Peter Biza, Tournefeuille (FR); Philip J. Jones, Woodstock, GA (US)

(73) Assignee: Imerys USA, Inc., Roswell, GA (US)

( * ) Notice: Subject to any disclaimer, the term of this patent is extended or adjusted under 35 U.S.C. 154(b) by 0 days.

(21) Appl. No.: 15/543,123

(22) PCT Filed: Jan. 12, 2016

(86) PCT No.: PCT/US2016/012965
§ 371 (c)(1),
(2) Date: Jul. 12, 2017

(87) PCT Pub. No.: WO2016/115078
PCT Pub. Date: Jul. 21, 2016

(65) Prior Publication Data
US 2017/0368096 A1    Dec. 28, 2017

Related U.S. Application Data

(60) Provisional application No. 62/102,887, filed on Jan. 13, 2015.

(51) Int. Cl.
*A61K 33/06* (2006.01)
*B01J 20/12* (2006.01)
(Continued)

(52) U.S. Cl.
CPC ............ *A61K 33/06* (2013.01); *A61K 9/0095* (2013.01); *B01J 20/12* (2013.01);
(Continued)

(58) Field of Classification Search
CPC ....... A61K 33/06; A61K 9/0095; B01J 20/12; B01J 20/28004; B01J 20/28059; C02F 1/281; C02F 2303/04
See application file for complete search history.

(56) References Cited

U.S. PATENT DOCUMENTS 3,224,892 A    12/1965   Hemstock
5,537,934 A     7/1996   Jensen et al.
(Continued)

OTHER PUBLICATIONS

International Search Report and Written Opinion dated Mar. 18, 2016, in International Application No. PCT/US2016/012965 (10 pgs.).
(Continued)

*Primary Examiner* — Trevor Love
(74) *Attorney, Agent, or Firm* — Finnegan, Henderson, Farabow, Garrett & Dunner LLP

(57) ABSTRACT

A method of treating water to reduce or prevent bacterial infection in an aquatic organism may include administering a particulate kaolin clay to the water in a dosage sufficient to reduce the presence of at least one undesirable bacterial species present in the water, wherein the particulate kaolin clay has at least one property selected from: (a) a BET surface area of at least about 25 $m^2/g$; (b) a particle size distribution such that at least about 80% by weight of the particles of kaolin clay have an equivalent spherical diameter of less than 2 microns as measured by Sedigraph; and (c) a particle size distribution such that at least about 25% by weight of the particles of kaolin clay have an equivalent spherical diameter of less than 0.25 microns as measured by Sedigraph. The method may further include contacting an aquatic organism with the treated water.

9 Claims, 5 Drawing Sheets

(51) Int. Cl.
*B01J 20/28* (2006.01)
*C02F 1/28* (2006.01)
*A61K 9/00* (2006.01)

(52) U.S. Cl.
CPC ... *B01J 20/28004* (2013.01); *B01J 20/28059* (2013.01); *C02F 1/281* (2013.01); *C02F 2303/04* (2013.01)

(56) References Cited

U.S. PATENT DOCUMENTS

| | | |
|---|---|---|
| 6,312,511 B1 | 11/2001 | Bilimoria et al. |
| 2004/0110885 A1 | 6/2004 | Husband et al. |
| 2009/0208750 A1 | 8/2009 | Costantin et al. |
| 2013/0323209 A1 | 12/2013 | Sung et al. |

OTHER PUBLICATIONS

Beck et al., "Kaolinitic clay protects against Flavobacterium columnare infection in channel catfish Ictalurus punctatus (Rafinesque)", Journal of Fish Diseases, Feb. 5, 2014, Retrieved from the Internet Mar. 11, 2016: <URL: http://onlinelibrary.wiley.com/doi/10.1111/jfd.12229/full>.

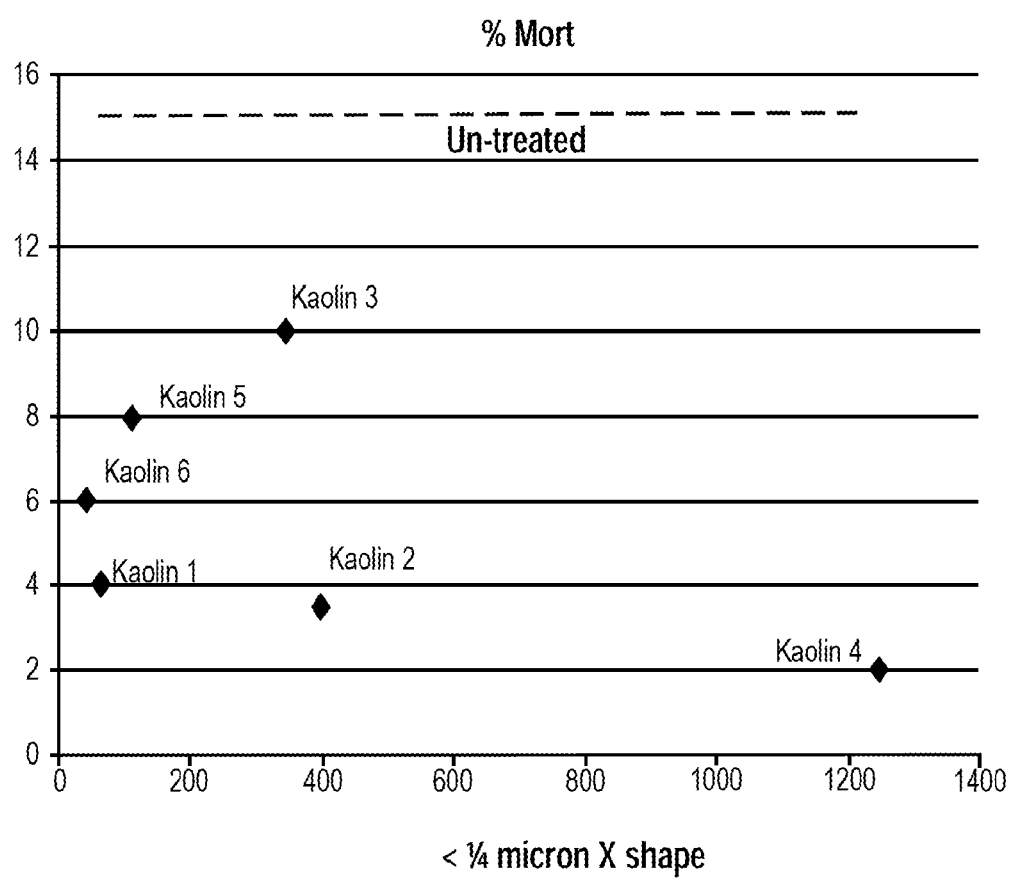

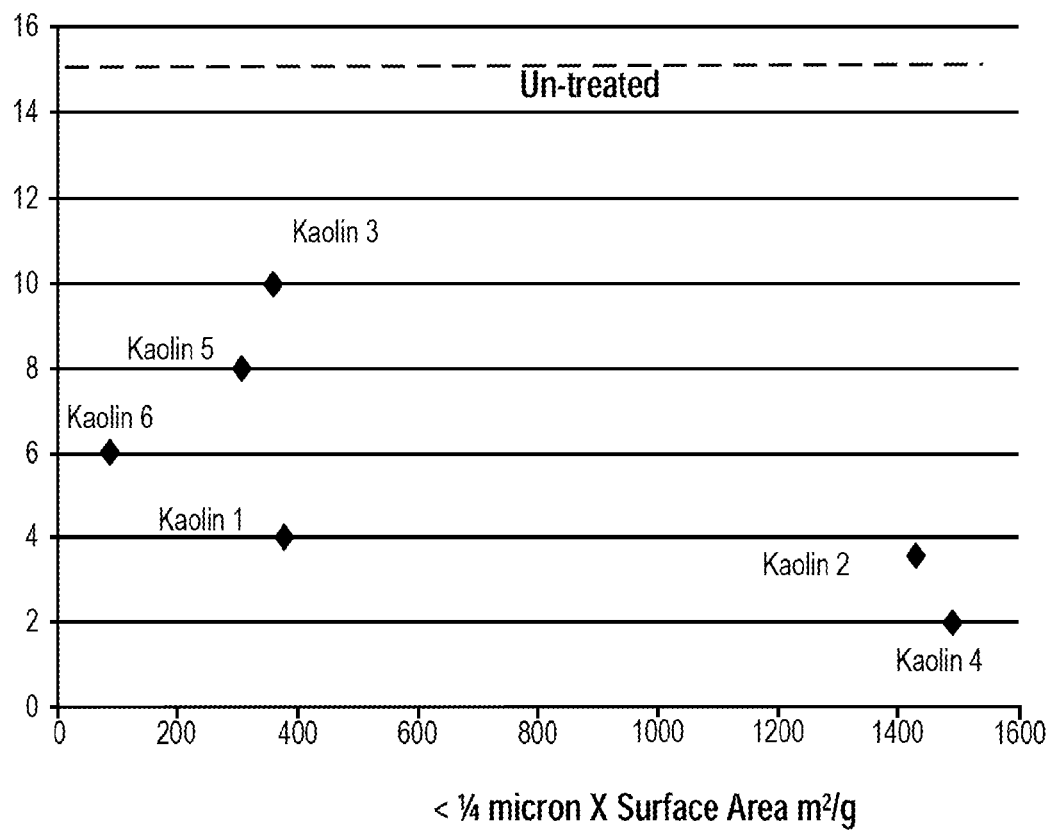

COMPOSITIONS AND METHODS FOR TREATING WATER

CLAIM FOR PRIORITY

This application is a U.S. national phase entry of International Application No. PCT/US2016/012965, filed Jan.12, 2016, which claims the benefit of priority of U.S. Provisional Patent Application No, 62/102,887, filed Jan. 13, 2015, to both of which this application claims the benefit of priority, and the entirety of the subject matter of both of which is incorporated herein by reference.

DESCRIPTION

Field of the Disclosure

The present disclosure relates to compositions and methods for treating water in fish farms and other aquaculture environments. More particularly, the disclosure relates to the application fine and/or platy of clays to water for bactericidal purposes.

Background

Columnaris disease is caused by the rod-shaped Gram-negative bacterium *Flavobacterium columnare*, an opportunistic pathogen which causes substantial mortality globally in freshwater farmed fish species. In particular, economically valuable channel catfish are have been found to be very susceptible to this pathogen.

Despite the importance of columnaris disease, there are few readily available means for its treatment or prevention. Antibiotics have been shown to exhibit some efficacy against columnaris disease, but the use of antibiotics in aquaculture is under increasing scrutiny and is becoming disfavored. Moreover, overuse of antibiotics in aquaculture in recent years has increased the risk of drug resistance acquisition by aquaculture pathogens such as those causing columnaris. Accordingly, there is a need for alternative preventatives and curatives for columnaris disease and other bacterial pathogens affecting cultured fish, that are not based on antibiotics.

Recent research has shown that treatment of water with kaolin clay can provide some efficacy against columnaris when applied to pond water (Beck et. al. 2014). In this study, Channel catfish were experimentally challenged with *Flavobacterium columnare* in untreated water or with water containing kaolin. Over the course of a 7-day study, kaolin treatment led to significantly improved survival as compared to untreated fish. However, the Beck study did not investigate the differing efficacy of different types of kaolin against columnaris.

Kaolin clay predominantly contains the mineral kaolinite, together with small concentrations of various other minerals such as smectites, mica, and iron compounds. Kaolinite is a hydrous aluminosilicate having the general formula $Al_2Si_2O_5(OH)_4$.

Kaolin clay can have a wide variety of particle sizes. For example, certain very coarse kaolins have a particle size distribution such that less than about 70% by weight of the particles, less than about 60% by weight of the particles, or less than about 50% by weight of the particles have a particle size of less than 2 microns as measured by Sedigraph®. In contrast, very fine kaolins can have a particle size distribution such that greater than 80% by weight of the particles, greater than 85% by weight of the particles, greater than 90%, or even greater than 95% by weight of the particles have a particle size of less than 2 microns as measured by Sedigraph.

Another way to view the size of a kaolin is by its fine particle content. For example, some very fine kaolins can have a particle size distribution such that greater than 20% by weight of the particles, greater than 25% by weight of the particles, greater than 30%, greater than 40%, or even greater than 50% by weight of the particles have a particle size of less than 0.25 microns as measured by Sedigraph. In contrast, coarse kaolins can have a particle size distribution such that less than 20% by weight of the particles, less than 15% by weight of the particles, or even less than 10% by weight of the particles have a particle size of less than 0.25 microns as measured by Sedigraph.

Kaolin clay can have a wide variety of particle shapes. For example, some blocky kaolins have shape factors of less than about 15, such as less than about 12, less than about 10, less than about 8, less than about 6, or even less than about 4. Other platy kaolins can have shape factors of greater than about 15, such as for example greater than about 20, greater than about 25, greater than about 30, greater than about 35, greater than about 40, greater than about 50, greater than about 70, or even greater than about 100.

Kaolin clays were formed in geological times by the weathering of the feldspar component of granite. Primary kaolin clays are those which are found in deposits at the site at which they were formed. For example, kaolin clays mainly of the primary type are obtained from deposits in South West England, France, Germany, Spain, and the Czech Republic. Sedimentary kaolin clays are those which were flushed out in geological times from the granite matrix in which they were formed, and were deposited in an area remote from their site of formation, generally in a basin formed in the surrounding strata. For example, kaolin clays obtained from deposits in the Southeastern United States and from Brazil are generally of the sedimentary type. Fine sedimentary kaolins having a particle size distribution after degritting such that about 80% by weight of the particles have an equivalent spherical diameter of less than 2 microns (by Sedigraph) are sometimes called "hard" kaolins. Fine sedimentary kaolins can also be referred to as "hard" kaolins.

SUMMARY

According to one aspect, a method of treating water to reduce or prevent bacterial infection in an aquatic organism may include administering a particulate kaolin clay to the water in a dosage sufficient to reduce the presence of at least one undesirable bacterial species present in the water, wherein the particulate kaolin clay has at least one property selected from: (a) a BET surface area of at least about 25 $m^2/g$; (b) a particle size distribution such that at least about 80% by weight of the particles of kaolin clay have an equivalent spherical diameter of less than 2 microns as measured by Sedigraph; and (c) a particle size distribution such that at least about 25% by weight of the particles of kaolin clay have an equivalent spherical diameter of less than 0.25 microns as measured by Sedigraph. The method may further include contacting an aquatic organism with the treated water In one embodiment, the method may include contacting a bacteria with the treated water, potentially allowing adsorption of the bacteria onto the kaolin.

In another aspect, the particulate kaolin clay can have a BET surface area of at least about 25 $m^2/g$. For example, the kaolin particulate clay can have a BET surface area of at least about 30 m²/g, such as at least about 40 m²/g. In one aspect, the particulate kaolin clay can have a BET surface area ranging from about 25 m²/g to about 40 m²/g.

In yet another aspect, the particulate kaolin clay can have a particle size distribution such that at least about 70% by weight of the particles of kaolin clay have an equivalent spherical diameter of less than 2 microns as measured by Sedigraph. For example, the particulate kaolin clay has a particle size distribution such that at least about 80%, at least about 85%, or at least about 90% by weight of the particles of kaolin clay have an equivalent spherical diameter of less than 2 microns as measured by Sedigraph.

In yet another aspect, the particulate kaolin clay can have a particle size distribution such that at least about 25% by weight of the particles of kaolin clay have an equivalent spherical diameter of less than 0.25 microns as measured by Sedigraph. For example, the particulate kaolin clay has a particle size distribution such that at least about 30%, at least about 40%, or at least about 50% by weight of the particles of kaolin clay have an equivalent spherical diameter of less than 0.25 microns as measured by Sedigraph.

In another aspect, the particulate kaolin clay has a combination of shape factor and particle size such that the product of its shape factor multiplied by the percentage by weight of the particles of kaolin clay having an equivalent spherical diameter of less than 0.25 microns as measured by Sedigraph has a value of at least about 300. For example, the product of the shape factor of the kaolin clay multiplied by the percentage by weight of the particles of kaolin clay having an equivalent spherical diameter of less than 0.25 microns as measured by Sedigraph can have a value of at least about 500, or at least about 1000.

In another aspect, the particulate kaolin clay has a combination of specific surface area and particle size such that the product of its specific surface area multiplied by the percentage by weight of the particles of kaolin clay having an equivalent spherical diameter of less than 0.25 microns as measured by Sedigraph has a value of at least about 600. For example, the product of the specific surface area of the kaolin clay multiplied by the percentage by weight of the particles of kaolin clay having an equivalent spherical diameter of less than 0.25 microns as measured by Sedigraph can have a value of at least about 800, or at least about 1000.

In another aspect, the particulate kaolin clay is administered to the water at a dosage ranging from about 0.01 g/L to about 3 g/L, such as from about 0.1 g/L to about 0.8 g/L. In another aspect, the particulate kaolin clay includes not more than 0.1% by weight dispersant.

In yet another aspect, the at least one undesirable bacterial species can include *Flavobacterium columnare*, *Edwardsiella Ictaluri*, and *Edwardsiella tarda*. In another aspect, the aquatic organism includes at least one fish, such as for example a fish selected from catfish, tilapia, carps, barbels and other cyprinids, salmon, sea bass, eels, mullet, bream, amberjack, grouper, perch, trout, sturgeon, or turbot, among others. In another aspect, the aquatic organism can include at least one crustacean, such as for example a crustacean selected from shrimp, prawns, lobster, crabs, or crayfish. In another aspect, the aquatic organism can include at least one shellfish, such as for example an oyster, a scallop, a mussel, or a clam.

It is to be understood that both the foregoing general description and the following detailed description are exemplary and explanatory only and are not restrictive of the invention.

BRIEF DESCRIPTION OF THE DRAWING

FIG. 4 is a graph representing the relative observed fish mortality after exposure to *F. Columnare* after treating with each of the kaolins assessed in the examples, compared with the product of shape factor times % fine kaolin particles having a particle size less than 0.25 microns for each kaolin.

FIG. 5 is a graph representing the relative observed fish mortality after exposure to *F. Columnare* after treating with each of the kaolins assessed in the examples, compared with the product of specific surface area times % fine kaolin particles having a particle size less than 0.25 microns for each kaolin.

DESCRIPTION OF EXEMPLARY EMBODIMENTS

Figure 1:
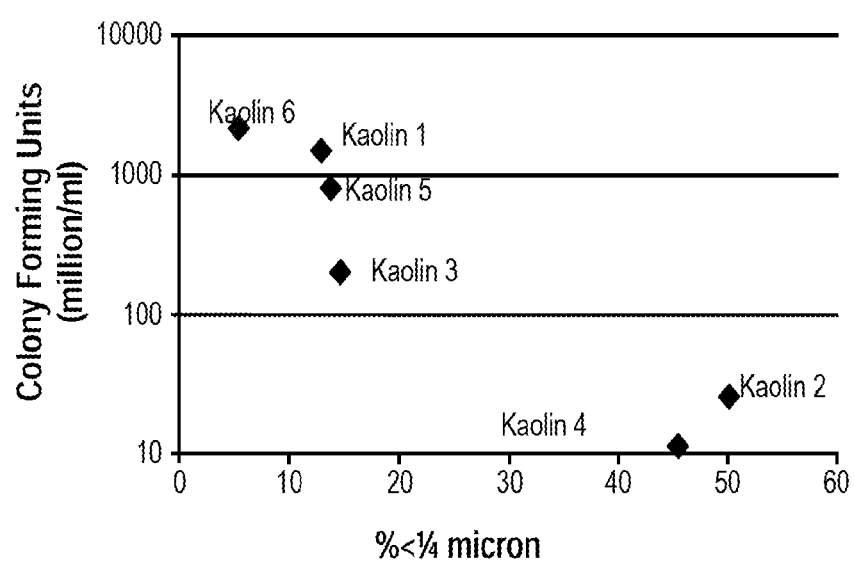
FIG. 1 is a graph representing the relative observed *F. Columnare* colony counts obtained after treating with each of the kaolins assessed in the examples, compared with the content of fine kaolin particles having a particle size less than 0.25 microns.

According to one aspect, the invention provides a method of treating water to reduce or prevent bacterial infection in an aquatic organism may include administering a particulate kaolin clay to the water in a dosage sufficient to reduce the presence of at least one undesirable bacterial species present in the water, wherein the particulate kaolin clay has at least one property selected from: (a) a BET surface area of at least about 25 m²/g; (b) a particle size distribution such that at least about 80% by weight of the particles of kaolin clay have an equivalent spherical diameter of less than 2 microns as measured by Sedigraph; and (c) a particle size distribution such that at least about 25% by weight of the particles of kaolin clay have an equivalent spherical diameter of less than 0.25 microns as measured by Sedigraph. The method may further include contacting an aquatic organism with the treated water.

As will be appreciated by those skilled in the art, the particle size distribution of a particulate material such as the kaolin clay may be determined by measuring the sedimentation speeds of the dispersed particles of the particulate material under test through a standard dilute aqueous suspension using a SEDIGRAPH® instrument (e.g., SEDIGRAPH 5100® obtained from Micromeritics Corporation, USA). The size of a given particle may be expressed in terms of the diameter of a sphere of equivalent diameter (i.e., the "equivalent spherical diameter" or esd), which sediments through the suspension, which may be used to characterize the particulate material. The SEDIGRAPH records the percentage by weight of particles having an esd less than a particular esd value, versus that esd value.

In one another aspect, the particulate kaolin clay can have a particle size distribution such that at least about 70% by weight of the particles of kaolin clay have an equivalent spherical diameter of less than 2 microns as measured by Sedigraph. For example, the particulate kaolin clay has a particle size distribution such that at least about 80%, at least about 85%, or at least about 90% by weight of the particles of kaolin clay have an equivalent spherical diameter of less than 2 microns as measured by Sedigraph.

In yet another aspect, the particulate kaolin clay can have a particle size distribution such that at least about 25% by weight of the particles of kaolin clay have an equivalent spherical diameter of less than 0.25 microns as measured by Sedigraph. For example, the particulate kaolin clay has a particle size distribution such that at least about 30%, at least about 40%, or at least about 50% by weight of the particles of kaolin clay have an equivalent spherical diameter of less than 0.25 microns as measured by Sedigraph.

In another aspect, the particulate kaolin clay can have a shape factor of less than about 45, or less than about 30. For example, the shape factor may range from about 2 to about 35, from about 2 to about 20, or from about 5 to about 15.

A kaolin product of relatively high shape factor may be considered to be more "platey" than a kaolin product of low shape factor, which may be considered to be more "blocky." "Shape factor" as used herein is a measure of an average value (on a weight average basis) of the ratio of mean particle diameter to particle thickness for a population of particles of varying size and shape, as measured using the electrical conductivity method and apparatus described in GB No. 2,240,398, U.S. Pat. No. 5,128,606, EP No. 0 528 078, U.S. Pat. No. 5,576,617, and EP 631 665, and using the equations derived in these publications. For example, in the measurement method described in EP No. 0 528 078, the electrical conductivity of a fully dispersed aqueous suspension of the particles under test is caused to flow through an elongated tube. Measurements of the electrical conductivity are taken between (a) a pair of electrodes separated from one another along the longitudinal axis of the tube, and (b) a pair of electrodes separated from one another across the transverse width of the tube, and by using the difference between the two conductivity measurements, the shape factor of the particulate material under test is determined. "Mean particle diameter" is defined as the diameter of a circle, which has the same area as the largest face of the particle.

In one aspect, the particulate kaolin clay has a combination of shape factor and particle size such that the product of its shape factor multiplied by the percentage by weight of the particles of kaolin clay having an equivalent spherical diameter of less than 0.25 microns as measured by Sedigraph has a value of at least about 300. For example, the product of the shape factor of the kaolin clay multiplied by the percentage by weight of the particles of kaolin clay having an equivalent spherical diameter of less than 0.25 microns as measured by Sedigraph can have a value of at least about 500, or at least about 1000.

BET surface area refers to the technique for calculating specific surface area of physical absorption molecules according to Brunauer, Emmett, and Teller ("BET") theory. BET surface area may be measured by any appropriate measurement technique. In one aspect, BET surface area can be measured with a Gemini III 2375 Surface Area Analyzer, using pure nitrogen as the sorbent gas, from Micromeritics Instrument Corporation (Norcross, Ga., USA).

In another aspect, the particulate kaolin clay can have a BET surface area of at least about 25 $m^2/g$. For example, the kaolin particulate clay can have a BET surface area of at least about 30 $m^2/g$, such as at least about 40 $m^2/g$. In one aspect, the particulate kaolin clay can have a BET surface area ranging from about 25 $m^2/g$ to about 40 $m^2/g$.

In another aspect, the particulate kaolin clay is administered to the water at a dosage ranging from about 0.01 g/L to about 3 g/L, such as for example from 0.1 g/L to about 1 g/L, from about 0.1 g/L to about 0.8 g/L, or from about 0.05 g/L to about 0.5 g/L.

In another aspect, the particulate kaolin clay includes not more than 0.1% by weight dispersant.

In yet another aspect, the at least one undesirable bacterial species can include *Flavobacterium columnare*. In another aspect, the aquatic organism includes at least one fish, such as for example a fish selected from catfish, tilapia, carp, salmon, sea bass, eels, mullet, bream, amberjack, grouper, perch, trout, sturgeon, or turbot, among others. In another aspect, the aquatic organism can include at least one crustacean, such as for example a crustacean selected from shrimp, prawns, lobster, crabs, or crayfish. In another aspect, the aquatic organism can include at least one shellfish, such as for example an oyster, a scallop, a mussel, or a clam.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, examples of certain embodiments of the present disclosure are given below.

EXAMPLES

The following examples assessed the effectiveness of six different kaolin clays when used to treat water for *F. columnare* bacteria. The particle size and shape factor characteristics of the six kaolins tested are summarized in TABLE 1 below.

TABLE 1

| Sample # | <2 μm | <0.5 μm | <0.25 μm | Shape Factor |
|---|---|---|---|---|
| Kaolin 1 | 60.5 | 27.0 | 12.9 | 4.6 |
| Kaolin 2 | 90.3 | 76.5 | 50.1 | 8.4 |
| Kaolin 3 | 55.5 | 30.5 | 14.7 | 23.2 |
| Kaolin 4 | 85.8 | 66.7 | 45.5 | 27.4 |
| Kaolin 5 | 62.4 | 32.1 | 13.8 | 8.2 |
| Kaolin 6 | 48.6 | 16.9 | 5.5 | 7.4 |

Twenty fingerling channel catfish (weighing approximately 5 g each on average) were stocked into an 18-L tank containing 10 L of filtered water. Water was provided through an Ultra-Low-Flow water delivery system at a rate of 29.1 mL/min. Fish were not fed the first day after challenge, but offered pelleted catfish feed (35% protein, 2.5% fat; Delta Western) on day 2 and throughout the rest of the study.

Fish were experimentally challenged with the virulent *F. columnare* isolate LSU-066. The isolate was retrieved from a glycerol stock preserved at 80° C. and streaked on Ordal's medium (Anacker & Ordal 1959). After 48 h, the isolate was dislodged from the agar using a sterile cotton swab and inoculated into 5 mL of *F. columnare* growth medium (FCGM; Farmer 2004). This suspension was incubated at 28° C. for 24 h and was used to inoculate 1 L of FCGM. The inoculated 1 L of broth was incubated for 24 h at 28° C. in an orbital shaker incubator set at 200 rpm; when the bacterial growth reached an absorbance of 0.75 at 550 nm, the flask was removed and placed on a stir plate at room temperature. Fish were challenged by adding 5 mL of the bacterial stock to each 10-L tank, with the exposed dose calculated to be $6.2 \times 10^6$ CFU/mL. Fish were observed twice daily to assess mortality.

In the exemplary kaolin treatments, 1 g/L kaolin was slowly added to the water near the airstone to facilitate mixing within the tank. In kaolin-treated tanks, kaolin was added to water 5 min prior to challenge with *F. columnare* to allow sufficient mixing time and the ultra-low flow was initiated. The concentration of kaolin was selected based on previous reports demonstrating that this dose was well tolerated in rainbow trout. The duration of the challenge experiment was 7 days.

In another test done in vitro the kaolin sample was added to a water containing around 9000 mio units per litre *Flavobacterium columnaris*. After allowing sufficient mixing time the kaolin was removed by centrifugation and the bacteria remaining in the supernatant were counted. The lower the bacteria count in the supernatant is, the more efficient bacteria were removed by the kaolin sample. As shown in FIG. 1 the relative observed *F. Columnare* colony counts obtained after treating with each of the kaolins assessed varied greatly depending on the particle size of the kaolin. In particular, it was surprisingly observed that kaolins having a high content of very fine particles having a particle size less than 0.25 microns display a higher efficacy against *F. columnare*.

Figure 2:
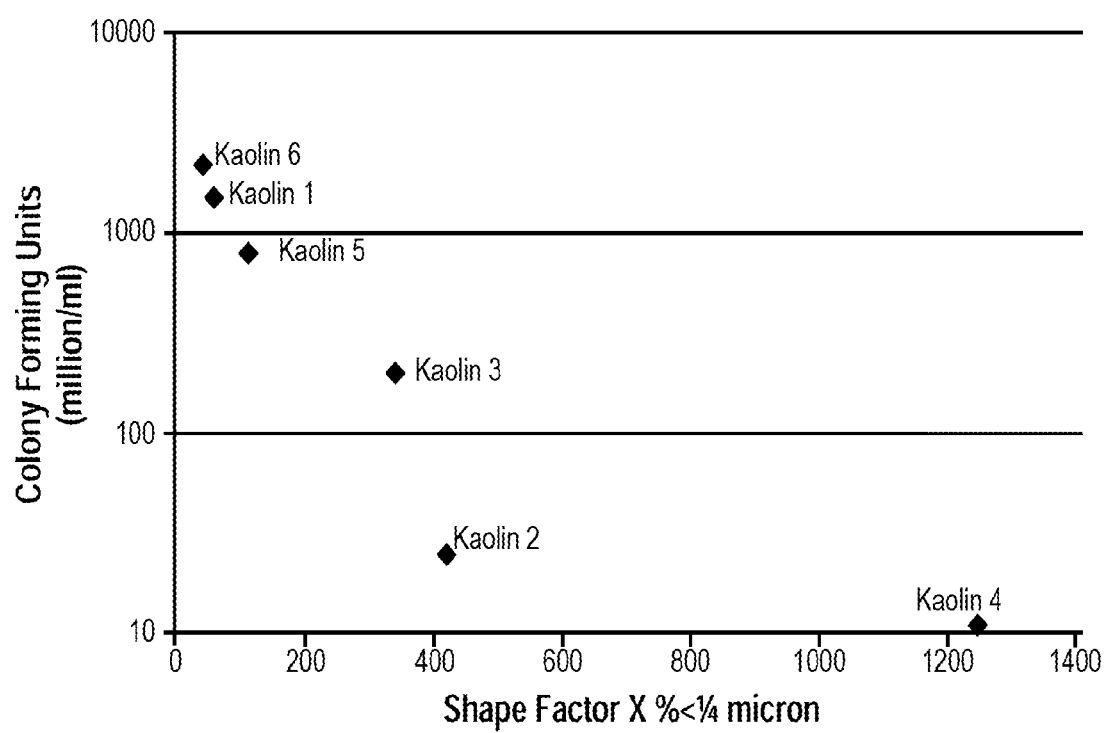
FIG. 2 is a graph representing the relative observed *F. Columnare* colony counts obtained after treating with each of the kaolins assessed in the examples, compared with the product of shape factor times % fine kaolin particles having a particle size less than 0.25 microns for each kaolin.

As illustrated in FIG. 2, there is an even greater dependence of observed *F. Columnare* colony counts when shape factor is also considered in addition to fine particle content by multiplying the shape factor of the kaolin by its fine particle content (<0.25 micron content). Efficacy against *F. columnaris* was suppressed to a surprisingly large degree when the water was treated with a very fine and platy kaolin clay, as shown by the very low colony count after treatment with kaolin 4.

Figure 3:
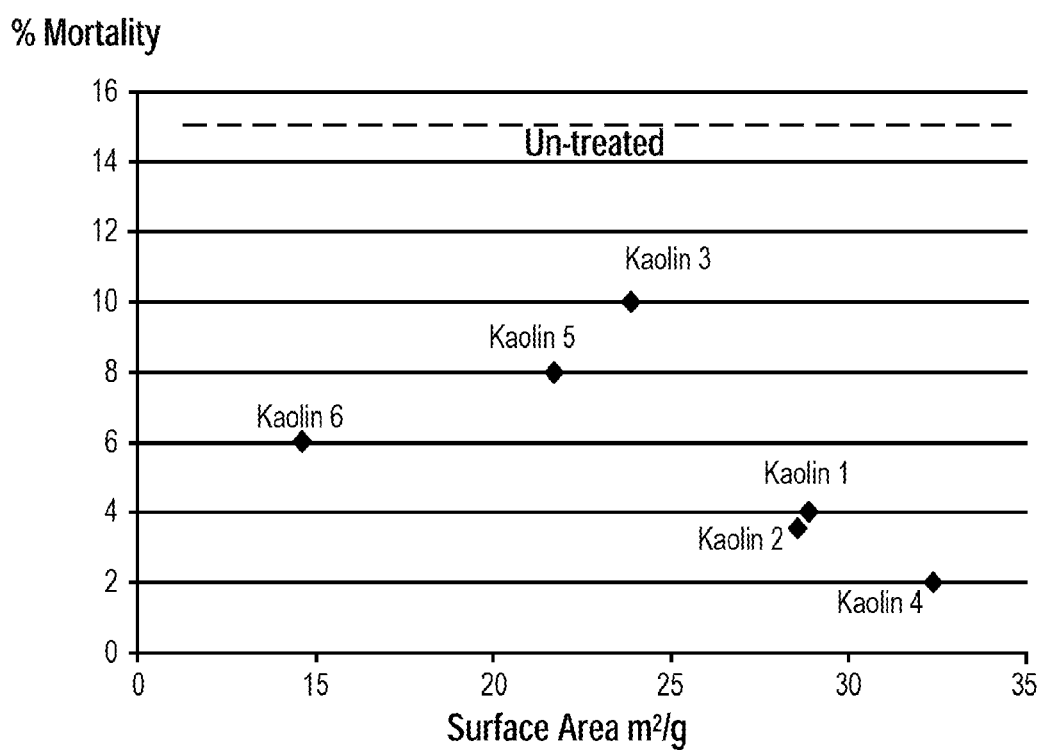
FIG. 3 is a graph representing the relative observed fish mortality after exposure to *F. Columnare* after treating with each of the kaolins assessed in the examples, compared with the BET surface area for each kaolin.

As shown in FIG. 3, the efficacy against *F. columnaris* in colony count experiments also correlates to a decrease in fish mortality when fine kaolin clays are used. FIG. 3. Illustrates the relative observed fish mortality after exposure to *F. Columnare* after treating with each of the kaolins assessed compared with the BET surface area for each kaolin. BET surface area is inversely correlated to the particle size of a kaolin, so the high BET surface area kaolins, so the higher BET surface area kaolins correspond to the same fine particle samples displaying efficacy in the colony count experiments.

As shown in FIG. 4, the efficacy against *F. columnaris* in fish mortality experiment also correlates to a decrease in fish mortality when fine and platy clays are used. FIG. 4. Illustrates the relative observed fish mortality after exposure to *F. Columnare* after treating with each of the kaolins assessed compared with the product of shape factor and % fine particles for each kaolin. As shown in FIG. 5, the relative observed fish mortality after exposure to *F. Columnare* after treating with each of the kaolins assessed compared with the product of specific surface area and % fine particles for each kaolin.

What is claimed is:

1. A method of treating water to reduce or prevent bacterial infection in a fish, the method comprising:
    administering a particulate kaolin clay to the water in a dosage sufficient to reduce the presence of at least one undesirable bacterial species present in the water;
    wherein the particulate kaolin clay comprises:
        (a) a BET surface area ranging from about 25 $m^2/g$ to about 40 $m^2/g$;
        (b) a particle size distribution such that at least about 80% by weight of the particles of kaolin clay have an equivalent spherical diameter of less than 2 microns as measured by Sedigraph; and
        (c) a particle size distribution such that at least about 50% by weight of the particles of kaolin clay have an equivalent spherical diameter of less than 0.25 microns as measured by Sedigraph; and
    contacting a fish with the water,
    wherein the particulate kaolin clay is administered to the water at a dosage ranging from about 0.01 g/L to about 3 g/L,
    wherein the shape factor of the kaolin clay multiplied by the percentage by weight of the particles of kaolin clay having an equivalent spherical diameter of less than 0.25 microns as measured by Sedigraph has a valve of at least about 1000, and
    wherein the specific surface area of the kaolin clay multiplied by the percentage by weight of the particles of kaolin clay having an equivalent spherical diameter of less than 0.25 microns as measured by Sedigraph has a value of at least about 600.

2. The method of claim 1, wherein the particulate kaolin clay has a particle size distribution such that at least about 85% by weight of the particles of kaolin clay have an equivalent spherical diameter of less than 2 microns as measured by Sedigraph.

3. The method of claim 1, wherein the particulate kaolin clay has a particle size distribution such that at least about 90% by weight of the particles of kaolin clay have an equivalent spherical diameter of less than 2 microns as measured by Sedigraph.

4. The method of claim 1, wherein specific surface area of the kaolin clay multiplied by the percentage by weight of the particles of kaolin day having an equivalent spherical diameter of less than 0.25 microns as measured by Sedigraph has a value of at least about 1000.

5. The method of claim 1, wherein the particulate kaolin clay is administered to the water at a dosage ranging from about 0.1 g/L to about 0.8 g/L.

6. The method of claim 1, wherein the particulate kaolin clay includes not more than 0.1% by weight dispersant.

7. The method of claim 1, wherein the at least one undesirable bacterial species includes *Flavobacterium columnare*.

8. The method of claim 1, wherein the fish is selected from catfish, tilapia, carp, salmon, sea bass, eels, mullet, bream, amberjack, grouper, perch, trout, sturgeon, or turbot.

9. The method of claim 1, wherein the kaolin is a sedimentary kaolin.

* * * * *